(12) United States Patent
Carli et al.

(10) Patent No.: US 6,355,273 B1
(45) Date of Patent: Mar. 12, 2002

(54) PHARMACEUTICAL COMPOSITIONS IN FORM OF POLYMERIC MICROPARTICLES OBTAINED BY EXTRUSION AND SPHERONIZATION

(75) Inventors: Fabio Carli; Massimo Bresciani; Tiziana Canal, all of Trieste; Paolo Gambini, Muggia, all of (IT)

(73) Assignee: Eurand International, S.p.A. (IT)

( * ) Notice: Subject to any disclaimer, the term of this patent is extended or adjusted under 35 U.S.C. 154(b) by 0 days.

(21) Appl. No.: 09/601,642

(22) Filed: Aug. 4, 2000

(30) Foreign Application Priority Data

Feb. 6, 1998 (IT) .......................... MI98A0233

(51) Int. Cl.$^7$ .............. A61K 9/14; A61K 9/16; A61K 47/30
(52) U.S. Cl. .............. 424/489; 424/490; 514/772.3
(58) Field of Search ................. 424/489, 490; 514/772.3

(56) References Cited

U.S. PATENT DOCUMENTS

| | | | | |
|---|---|---|---|---|
| 4,086,346 A | * | 4/1978 | Bocker et al. | 424/253 |
| 5,275,824 A | * | 1/1994 | Carli et al. | 424/490 |
| 5,350,584 A | * | 9/1994 | McClelland et al. | 424/501 |
| 6,063,313 A | * | 5/2000 | Briskin et al. | 264/15 |

* cited by examiner

Primary Examiner—Thurman K Page
Assistant Examiner—Rachel M. Bennett
(74) Attorney, Agent, or Firm—Thompson Hine LLP

(57) ABSTRACT

Process for the preparation of pharmaceutical compositions comprising one or more polymers and one or more drugs by the extrusion and spheronization technique, wherein polymers belong to the group of the cross-linked amphiphilic polymers.

15 Claims, 1 Drawing Sheet

PHARMACEUTICAL COMPOSITIONS IN FORM OF POLYMERIC MICROPARTICLES OBTAINED BY EXTRUSION AND SPHERONIZATION

This application is a 371 of PCT/EP99/00781 filed Feb. 5, 1999.

PRIOR ART

Processes for the preparation of pharmaceutical compositions having microparticles form, comprising the mixing of an active principle with suitable excipients, the extrusion through a mesh in order to form cylindrical filaments and the subsequent spheronization are known.

The fundamental problem of the technique of these processes is that the mixture which is extruded must be sufficiently plastic to allow the stability of the cylindrical filaments form and sufficiently malleable to transform said cylindrical filaments in spherical particles by spheronization. It is possible to use several machines to obtain spherical microparticles: for example, high efficiency granulators, frontal or axial extruders, fluid bed rotogranulators, radial extruders, coaxial double screw extruders, etc. However, notwithstanding the fact that the used plants are of different kind, the known extrusion/spheronization techniques are based on the use of mixtures containing microcrystalline cellulose (AVICELL™) in percentages ranging from 10 to 20%, whose properties allow the conferring and the maintainment of the necessary plasticity and malleability during the whole process (R. E. Connor and J. B. Schwartz, Drug Dev. Ind. Pharm. 2, 1837, 1985). In order to overcome this problem different techniques which, however, show notable drawbacks have been proposed.

The U.S. Pat. No. 5,049,394 proposes to decrease the microcrystalline cellulose percentages using mixtures of solvents (for example water/ethanol) in spite of water only in order to moisten the dusts.

The U.S. Pat. No. 5,350,584 suggests the use of ionic resins in order to give the desired plasticity to the material to extrude and spheronize. Both the solutions present some applicative limitations because it may be necessary, for some kinds of formulations or in case of incompatibility, to avoid the use of solvents or ionized materials.

A solution proposed to overcome the problems related to the plasticity of the mixture to extrude considers the melting at a suitable temperature of the mixture itself (WO 96/25149 and WO 96/25151). The limitation of this solution lies in the necessity to use thermostable materials and active principles.

Other solutions consider the use of high amounts (to 50%) of plasticizing substances (JP 2527107) allowing to keep plastic the mass to extrude. Such technique strongly limits the amount of active principle which may be introduced in the mass to extrude and moreover it can cause compatibility problems among the materials.

SUMMARY

Now we have unexpectedly found that the problems of the prior art are solved using, for the preparation of microparticles by extrusion and spheronization, compositions comprising cross-linked amphiphilic polymers.

Therefore the present invention relates to a process for the preparation of pharmaceutical compositions in form of polymeric microparticles comprising:

a) the preparation of a homogeneous mixture of substances in powder form to which a liquid to a pasty consistence is added;

b) the extrusion of the mixture of the step a) through a perforated mesh in order to obtain cylindrical filaments;

c) the spheronization of the cylindrical filaments of the step b) in order to obtain microparticles in spherical form, and d) the drying of the microparticles of the step c), e) optionally drug is deposited on the surface of the microparticles, characterized in that said mixture of substances in powder form consists of one or more cross-linked amphiphilic polymers and optionally one or more drugs, excipients, a bioadhesive substance and/or a substance having high density.

The process according to the present invention shows several advantages with respect to the prior art because it does not ask for the presence of plasticizing, linking substances, solvents or linear polymers and it allows the incorporation of high percentages of drugs having different characteristics of solubility and wettability.

DETAILED DESCRIPTION OF THE INVENTION

Figure 1:
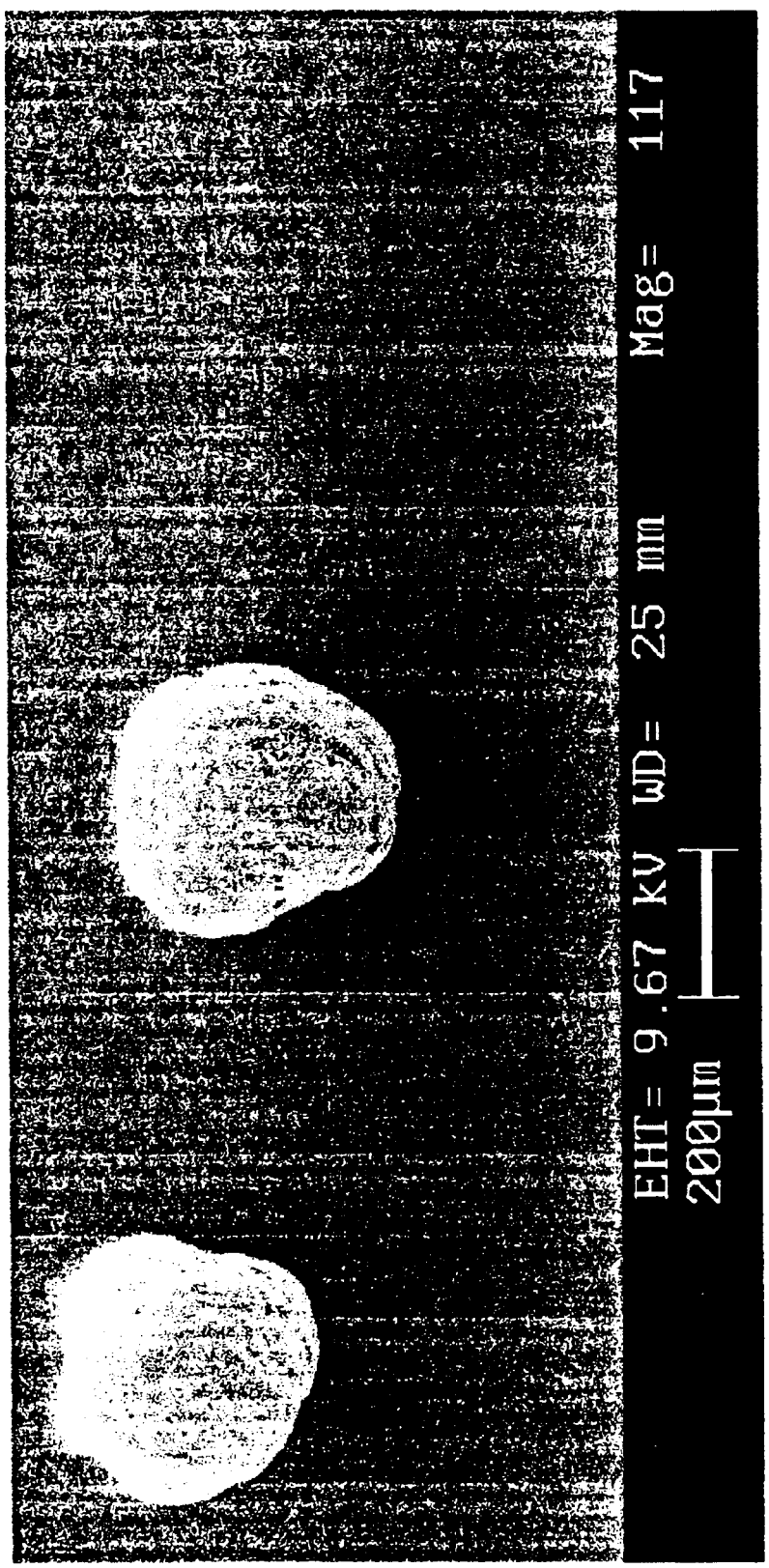
FIG. 1 represents the microparticles obtained by the example 6 procedure, determined by scanning electron microscopy.

The process described in this invention relates to the production of pharmaceutical compositions in form of microparticles or spherical multiparticulates based on cross-linked amphiphilic polymers by the following steps:

a) the mixing of one or more cross-linked amphiphilic polymers with one or more active principles, when needed, and optionally other pharmaceutical excipients in order to obtain a uniform mixture in form of dry powder to which a suitable amount of liquid is added to obtain a pasty consistency;

b) the extrusion of the mixture obtained from the step a) through a perforated mesh in order to obtain cylindrical filaments having desired length and diameter;

c) the spheronization of the filaments in order to obtain a product in the form of spherical multiparticulates;

d) the drying of the product;

e) the optional depositing of a drug on the surface of the microparticles.

With the expression "spherical multiparticulate" we mean spherical or almost-spherical microparticles whose diameter size may range from about 100 μm to about 3 mm.

With the expression "cross-linked amphiphilic polymer" we mean a polymer showing characteristics of swellability in the whole pH range of aqueous solutions and also in solvents or solvent mixtures having different polarity characteristics. The polymers may be cross-linked either physically, through the interpenetration of the macromolecular meshes, or chemically, thus showing points of link among the macromolecular chains.

Significant but not limitative examples of such polymers comprise cross-linked polyvinyl pyrrolidone, sodium carboxymethylcellulose, sodium glycolate starch and dextrans. Optional excipients consist of dispersing, emulsifying, wetting or colouring agents.

With the expression "active principle" we mean any physiologically or pharmacologically acceptable substance, organic or inorganic, of natural or synthetic origin, producing systemic or local effects in living beings. The active principles which may be vehiculated by the microparticles of this invention comprise drugs acting on the central nervous system and on the peripheral nervous system, cardiovasculars, hypotensives, diuretics, anti-inflammatories, analgesics, antifebriles, antiasthmatics, bronchodilatators, antitussis, mucolytics, antibiotics, chemotherapeutic agents, antivirals, hormones, antineoplastics, immunosuppressants, immunostimulants, peptides, polypeptides, proteins, vaccines and so on.

Among the drugs which may be formulated according to the invention we may mention, for example:

ergot alkaloids and derivatives: dihydroergotamine, dihydroergotoxine, bromocriptine.

Analgesics and non steroidal anti-inflammatories, and their salts: diclofenac sodium, diclofenac hydroxyethyl pyrrolidine, diclofenac diethylamine, ibuprofen, flurbiprofen, ketoprofen, indomethacin, mefenamic acid, naproxen, nimesulide, piroxicam.

Antiarrhythmics: amiodarone, diisopyramide, propranolol, verapamil.

Antibacterials: amoxicillin, flucloxacillin, gentamicin, rifampicin, erythromycin, cephalosporins.

Antifungals and antipsoriatics: amphotericin, butoconazole nitrate, ketoconazole, econazole, etretinate, fluconazole, flucytosine, griseofulvin, itraconazole, miconazole, nystatin, sulconazole, tioconazole.

Antivirals: acyclovir, ganciclovir, AZT, protease inhibitors.

Antihypertensives: amlodipine, clonidine, diltiazem, felodipine, guanabenz acetate, isradipine, minoxidil, nicardipine hydrochloride, nimodipine, nifedipine, prazosin hydrochloride, papaverine.

Antidepressants: carbamazepine.

Antihistaminics: diphenhydramine, chlorpheniramine, pyrilamine, chlorcyclizine, promethazine, acrivastine, cinnarizine, loratadine, terfenadine.

Antineoplastics and immunosuppressants: cyclosporin, dacarbazine, etretinate, etoposide, lomustine, melphalan, mitomycin, mitoxantrone, paclitaxel, procarbazine, tamoxifen, taxol and derivatives, taxotere.

Anxiolytics, sedatives, hypnotics: alprazolam, bromazepam, diazepam, lorazepam, oxazepam, temazepam, sulpiride, triazolam.

β-Blockers: alprenolol, oxprenolol, pindolol, propranolol.

β-Agonists: salbutamol, salmeterol.

Cardiac and cardiovascolar inotropics: amrinone, digitoxin, digoxin, lanatoside C, medigoxin, ubidecarenone.

Corticosteroids: beclomethasone, betamethasone, budesonide, cortisone acetate, desoximethasone, dexamethasone, fludrocortisone acetate, flunisolide, hydrocortisone, methyiprednisone, triamcinolone.

Gastrointestinals and anti H2-histaminics: cimetidine, cisapride, domperidone, famotidine, loperamide, mesalazine, omeprazole, ondansetron hydrochloride, ranitidine.

hypolipidemics: bezafibrate, clofibrate, gemfibrozil, probucol, lovastatin.

Anti-anginals: amyl nitrate, glyceryl trinitrate, isosorbide dinitrate and mononitrate, pentaerythritol tetranitrate.

Central Action Drugs: for example nicotine.

Vitaminic and Nutritional Agents: betacarotene, vitamin A, Vitamin B2, Vitamin D and derivatives, vitamin E and derivatives, vitamin K.

Opioid Analgesics: codeine, dextropropoxyphene, diihydrocodeine, morphine, pentazocine, methadone.

Sexual Hormones: danazol, ethinyl estradiol, medroxyprogesterone acetate, methyltestosterone, norethisterone, norgestrel, estradiol, estriol, progesterone, stilbestrolo, diethylstilbestrol.

Peptidic, proteic or polysaccharidic molecules having different activity:

leuprolide and LH-RH analogues, calcitonin, glutathione, somatotropin (GT), somatostatin, desmopressin (DDAVP), interferon, molgramostin, epidermic growth factor (EGF), nervous growth factor (NGF), insulin, glucagon, toxins or toxoides (for example tetanus toxin), antigenic factors of proteic or polysaccharidic kind, heparin having low molecular weight, heparinoids.

The active principles may be uniformly distributed inside the microparticles or they may be deposited on the surface of the microparticles by techniques normally used in the pharmaceutical processes (for example, spray drying, coating in basins, and so on).

In the case that an active principle is distributed inside the microparticles, it ranges from about 0.1% to about 95% by weight of the microparticles.

A particular embodiment of this invention relates to the extrusion/spheronization of the active principles included and/or charged on cross-linked amphiphilic polymers according to the techniques disclosed in the Patents EP 0 371 431, U.S. Pat. No. 5.449.521, EP 0 364 944, U.S. Pat. No. 5,569,469, PCT IB96/00492.

In these cases composite materials consisting of active principle/cross-linked amphiphilic polymer, obtained by high energy comilling or solvent loading techniques, are extruded. An advantage of this particular application consists in the coupling between improved solubility and bioavailability of the active principle obtained by the techniques described in the cited Patents and the improved technological characteristics of the microparticles, which allows its immediate application without further formulative passages.

With the term "excipients" we mean substances commonly used in the pharmaceutical technique as linking, dispersing, emulsifying, wefting or colouring agents. Not exhaustive examples of such excipients may be found in "Handbook of Pharmaceutical Excipients", 2nd Edition, American Pharmaceutical Association, 1994.

A particular embodiment of this invention relates to the preparation of spherical multiparticulates to which selected excipients give the bioadhesiveness and/or high density characteristics according to what is disclosed in the Patent EP 0 526 862.

Among the substances suitable to give bioadhesiveness we may mention for example: sodium alginate, scleroglucan, chitosan, xanthan, silicone gel, and so on.

Among the substances suitable to give high density we may mention not exhaustively: aluminium oxide, titanium dioxide, iron oxide, calcium carbonate, barium sulfate, and so on.

With the expression "uniform mixture" we mean that the components of the mixture are uniformly dispersed in the formulation by a mixing process which assures the uniform distribution of each component.

A reasonable mixing time may range from 1 to 60 minutes using one of the mixing equipments normally used for the dry mixing of the powders (for example: "V", fixed body, rotating body, sigma mixers and so on).

With the term "liquid" we mean any liquid substance or mix (solution or emulsion) of liquids of normal pharmaceutical use able to moisten the powder mix, as for example water, aqueous solutions having different pH, organic solvents of normal pharmaceutical use (for example, alcohols, chlorinated solvents, and so on), oils. Among the oils which may be used we cite for example: natural oils, either saturated or unsaturated (olive, peanut, soybean, corn, coconut, palm, sesame and similar oils); semisynthetic and synthetic mono-, di- and triglycerides containing saturated and/or unsaturated fatty acids and their polyhydroxyethylated derivatives (caprico-caprilic triglycerides [Mygliol™, Captex™, Labrafac™, Lipo], saturated or unsaturated polyhydroxylated triglycerides of various kind [Labrafil™, Labrafac™ Hydro, Gelucire™]); liquid waxes (isopropyl myristate, isopropyl-caprinate, -caprylate, -laurate, -palmitate, -stearate); fatty acids esters (ethyl oleate, oleyl oleate); silicone oils; polyethylene glycols (PEG 200, PEG 400, PEG 600, PEG 1000, and so on); polyglycolic glycerides (for example Labrasol™); polyglycols (propylene glycol, tetraglycol, ethoxydiglycol (Transcutol™).

For example all the non ionic surfactants may be mentioned among the surfactants: sorbitan-esters of fatty acids (for example Span®, Arlacel®, Brij®), polyoxyethylenesorbitan esters of fatty acids (for example Tween®, Capmul®, Liposorb®), polypropylene oxide-polyethylene oxide (Poloxamer) copolymers, polyethylene glycol esters (PEG)-glycerol (Labrasol®, Labrafil®), PEG esters and long chain aliphatic acids or alcohols (for example Cremophor®), polyglycerid esters (Plurol®), saccharide and fatty acid esters (sucro-esters). Moreover, anionic surfactants (for example sodium lauryl sulfate, sodium stearate, sodium oleate) or cationic surfactants (for example tricetol), may be used as well as lecithins, phospholipids and their semi-synthetic or synthetic derivatives.

Moreover active principles and/or excipients may be dissolved, dispersed and/or emulsified in such liquids.

In a particular embodiment of the invention, the moistening liquid consists of an oil/surfactant system wherein the active principle optionally emulsified with an aqueous phase is dissolved or dispersed. The amount of liquid with respect to the solid used in the preparation of the mixture of the step a) ranges from 1 to 80% by weight.

The moistened mass is extruded through a perforated mesh in order to produce cylindrical filaments. The port of the meshes determines the diameter of the filaments. A port ranging from about 0.2 mm to about 3 mm may be used in this process. Preferably, in this process, the port ranges from about 0.4 mm to 2 mm. The extrusion may be carried out using screw, double screw, "sieve and basket" kind, "roll extruder", "ram extruder" extruders or any other pharmaceutically acceptable means to produce cylindrical filaments. In some particular embodiments of this invention a double screw coaxial extruder may be used.

The filaments obtained by extrusion may be directly stocked or spheronized.

The spheronization device consists of a hollow cylinder with a horizontal rotating plate. The filaments are broken in short segments which are transformed in spherical or quasi-spherical particles on the upper surface of the rotating plate at a velocity ranging from about 200 rpm to about 2,000 rpm.

The particles may be dried in any pharmaceutically acceptable way, such as for example the air drying or in a static condition or their combination. The particles are used as they are or they are coated to obtain granules to use in tablets, capsules, packets and other pharmaceutical formulations.

Unexpectedly, operating according to the present invention, the extruded mixture has physical characteristics which allow to maintain the cylindrical form of the extrusion filaments and to transform said filaments in spherical microparticles also without the addition of plasticizers, binders, solvents or linear polymers neither to the mixture nor to the moistening liquid, as described in the above techniques. This moreover allows to limit possible compatibility problems between the possibly incorporated active principle and the excipients. Moreover, the amphiphilic characteristics of the cross-linked polymers and their capacity to swell in the presence of physiological liquids, allow an improved dissolution velocity of the active principle. Moreover the obtained microparticles show good physical characteristics (for example, hardness, density, intraparticle porosity, and so on) which make them suitable for a direct use (for example, direct compression, encapsulation or distribution in packets).

The following Examples are reported for illustrative but not limitative aim of the invention.

EXAMPLE 1

Preparation of Microparticles Consisting of Explotab

For the preparation of this Example a double screw extruder is used having the following dimensional characteristics: screw diameter=30 mm, head length 10 diameters and a head equipped with a threader having hole diameter equal to 1 mm.

Said extruder is fed with Explotab™ (sodium glycolate starch, Mendell) in the form of powder having granulometry lower than 140 mesh; demineralized water is fed together with Explotab™.

The extrusion is carried out according to the following operative parameters:

Explotab flow rate: 6 kg/h
Demineralized water flow rate: 2.1 kg/h
Torsional stress: 17%
Extruder head temperature: 13° C.
Screw rotation velocity: 60 rpm.
Extrusion filaments having an excellent form stability are obtained.

Then said filaments are treated in a spheronizator having a velocity equal to 800 rpm for 3 minutes, obtaining a product in the form of microparticles which are dried in a stove at 70° C. for 12 hours.

The obtained microparticles show the following characteristics:

apparent density: 0.710 g/cm$^3$
diameter fraction ranging from 0.8 mm to 1.4 mm: 87%.

EXAMPLES 2 AND 3

The Example 1 is repeated with the difference that Kollidon Cl™ (cross-linked polyvinyl pyrrolidone, Basf) and Ac Di Sol™ (cross-linked sodium carboxymethyl cellulose, FMC) are respectively used and that one operates with a screw rotation velocity respectively equal to 140 rpm and 100 rpm, with torsional stress respectively equal to 30% and 15% and with a temperature of the extruder head respectively equal to 35° C. and 20° C.

The obtained microparticles show the following characteristics:

microparticles consisting of Kollidon Cl:
  apparent density: 0.496 g/cm$^3$
  diameter fraction ranging from 0.8 mm to 1.4 mm: 96%
microparticles consisting of Ac Di Sol:
  apparent density: 0.538 g/cm$^3$
  diameter fraction ranging from 0.8 mm to 1.4 mm: 92%

EXAMPLE 4

Preparation of Microparticles Consisting of a Mixture of Explotab and Kollidon CL A mixture consisting of 50% by weight of Explotab™ and 50% by weight of Kollidon Cl™, using a planetary mixer with a mixing time equal to 20 minutes is prepared.

The extrusion, the spheronization and the drying are carried out according to the Example 1, working with a torsional stress equal to 18%, with an extruder head temperature equal to 24° C. and with screw rotation velocity equal to 140 rpm. The obtained microparticles have the following characteristics:

apparent density: 0.598 g/cm$^3$
diameter fraction ranging from 0.8 mm to 1.4 mm: 91.6%.

EXAMPLES 5 AND 6

The Example 4 is repeated with the difference that the mixtures consist respectively of Explotab™ and Ac Di Sol™ and of Kollidon Cl™ and Ac Di SO™ (these products have been defined in the above Examples).

The extrusion, the spheronization and the drying are carried out according to the Example 1, working with a torsional stress respectively equal to 15% and 25%, with an extruder head temperature respectively equal to 22° C. and 35° C. and with rotation velocity of the screws respectively equal to 80 rpm and 140 rpm. Moreover, the mixture Explotab/Ac Di Sol has been extruded using a 0.4 mm threader and characterized using the scanning electron microscopy (SEM) (FIG. 1).

The obtained microparticles have the following characteristics:

microparticles consisting of Explotab and Ac Di Sol:
  apparent density: 0.596 g/cm$^3$
  diameter fraction ranging from 0.8 mm to 1.4 mm: 87% (see photo).
Microparticles consisting of Kollidon Cl and Ac Di Sol:
  apparent density: 0.521 g/cm$^3$
  diameter fraction ranging from 0.8 mm to 1.4 mm: 95.6%.

EXAMPLE 7

The Example 1 is repeated feeding the Kollidon ClM™ as polymer and a 50/50 w/o emulsion as wetting liquid, wherein the oily part consists of 95% Labrafac Hydro 9™ (polyhydroxylated triglyceride) and of 5% Tween 80™ (polysorbate 80, Sigma).

The mixture is extruded through a threader having a diameter of the holes equal to 0.75 mm operating according to the following parameters:

Kollidon ClMTM flow rate: 3.9 kg/h
Wetting liquid flow rate: 38.8 kg/h
Torsional stress: 22%
Extruder head temperature: 35° C.
Screw rotation velocity: 140 rpm.

The spheronization and the drying are carried out according to the Example 1.

A product is obtained consisting of microparticles having the following characteristics:

apparent density: 0.488 g/cm$^3$
fraction ranging from 0.5 mm to 0.9 mm: 88.2%.

EXAMPLE 8

Preparation of Microparticles Containing Nifedipine as an Active Substance

A mixture of nifedipine and Kollidon CLM™ (defined in the above Examples) in a ratio equal to 1/3 by weight is comilled obtaining the mixture in the form of powder having the 100% of granulometry lower than 50 $\mu$m.

The mixture is moistened using as liquid demineralized water containing Kollidon 25™ (polyvinyl pyrrolidone, Basf) in a solution 3% w/w. The extrusion is carried out forcing the moistened mass through a threader having diameter of the holes equal to 1 mm.

The operative parameters are the following:

Powder flow rate: 4.5 kg/h
Liquid flow rate: 4.1 kg/h
Torsional stress: 27%
Head temperature: 46° C.
Screw rotation velocity: 140 rpm.

The extrusion filaments are then processed in a spheronizator adjusted at a velocity equal to 1,000 rpm for 2 minutes. The obtained microparticles are then dried in a fluid bed for 2 hours to a maximum temperature equal to 59° C. At the end of the drying the product is discharged and it is mechanically screened separating the fraction ranging from 0.7 mm to 1.2 mm, which forms the 91% by weight of the product.

The microparticles have an apparent density equal to 0.556 g/cm$^3$.

The dissolution velocity of the so obtained pellets, determined using the USP Paddle method (Apparatus 2), in sink conditions in pH 7.5 buffer, is reported.

| Time (min.) | Released % |
|---|---|
| 2 | 34.9 |
| 5 | 56.0 |
| 10 | 77.7 |
| 20 | 89.3 |
| 30 | 98.6 |

EXAMPLE 9

The Example 8 is repeated with the difference that the mixture consists of nifedipine and Explotab™ (defined in the above Examples) in a ratio 1/5 by weight.

The obtained microparticles have the following characteristics:

apparent density: 0.544 g/cm$^3$ diameter fraction ranging from 0.8 mm to 1.4 mm: 87.5%.

EXAMPLE 10

Preparation of Microparticles Containing Nifedipine as an Active Substance

An activated system obtained by loading nifedipine by solvent, and Kollidon CLM™ (defined in the above Examples) are mixed in a ratio 1/5 by weight in the form of powder having 100% granulometry lower than 50 µm.

The mixture is moistened using as wetting liquid demineralized water containing Kollidon 25™ (polyvinyl pyrrolidone) in a 2% solution. The extrusion is carried out forcing the humid mass through a threader having diameter of the holes equal to 1 mm. The operative parameters are the following:

Powder flow rate: 3.3 kg/h
Liquid flow rate: 2.2 kg/h
Torsional stress: 39%
Head temperature: 55° C.
Screw rotation velocity: 140 rpm.

The extrusion filaments are then processed in a spheronizator adjusted at a velocity equal to 1,000 rpm for 2 minutes. The obtained microparticles are then dried in a fluid bed for 2 hours to a maximum temperature equal to 59° C. At the end of the drying the product is mechanically screened separating the fraction ranging from 0.7 mm to 1.2 mm, which forms the 94.2% by weight of the product. The microparticles have an apparent density equal to 0.511 g/cm$^3$. The dissolution velocity of the so obtained pellets, determined using the USP Paddle method (Apparatus 2), in sink conditions in a pH 7.5 buffer, is reported.

| Time (min.) | Released % |
|---|---|
| 3 | 52.2 |
| 5 | 69.5 |
| 15 | 81.6 |
| 30 | 88.8 |
| 60 | 90.6 |

EXAMPLE 11

Preparation of Microparticles Containing Nicardipine as an Active Substance Kollidon CLM as a Carrier and Barium Sulfate as a High Density Substance.

The Example 8 is repeated with the mixture in the form of powder consisting of barium sulfate, nicardipine and Kollidon CLM™ (ratio 1/3).

The extrusion is carried out according to the following operative parameters:

Powder flow rate: 4.1 kg/h
Liquid flow rate: 3.05 kg/h
Torsional stress: 35%
Head temperature: 38° C.
Screw rotation velocity: 140 rpm.

The extrusion filaments are then treated in a spheronizator adjusted at a velocity equal to 1,000 rpm for 4 minutes. The obtained microparticles are then dried in a fluid bed for 2 hours to a temperature equal to 75° C. At the end of the drying the product is mechanically screened separating the fraction ranging from 0.5 mm to 1.2 mm, which forms the 92.15% by weight of the product.

The microparticles have the following quantitative composition:

| | |
|---|---|
| Barium sulfate | 10.00% by weight |
| Nicardipine | 22.50% by weight |
| Kollidon CLM | 67.50% by weight |

The microparticles have density characteristics at the pouring equal to 0.756 g/cm$^3$.

What is claimed is:

1. Process for the preparation of pharmaceutical compositions in form of polymeric microparticles comprising a drug and a cross-linked amphiphilic polymer, said process comprising the steps of:

a) preparing a homogeneous mixture of substances in powder form to which a liquid is added to obtain a pasty consistency, wherein said mixture comprises one or more cross-linked amphiphilic polymers;

b) extruding the mixture of step a) through a perforated mesh in order to obtain cylindrical filaments;

c) spheronizing the cylindrical filaments of step b) in order to obtain microparticles in spherical form, and d) drying the microparticles of step c).

2. Process as claimed in claim 1, wherein said cross-linked amphiphilic polymers are selected from the group consisting of cross-linked polyvinyl pyrrolidone, sodium carboxymethyl cellulose, sodium glycolate starch and dextrans.

3. Process as claimed in claim 1, wherein said drug is selected from the group consisting of drugs acting on the central nervous system and on the peripheral nervous system, cardiovasculars, hypotensives, diuretics, antiinflammatories, analgesics, antifebriles, antiasthmatics, bronchodilatators, antitussis, mucolytics, antibiotics, chemotherapeutic agents, antivirals, hormones, antineoplastics, immunosuppressants, immunostimulants, peptides, polypeptides, proteins and vaccines.

4. Process as claimed in claim 1 wherein said drug is uniformly distributed inside the microparticles.

5. Process as claimed in claim 4, wherein the drug ranges from 0.1 to 95% by weight with respect to the microparticles.

6. Process as claimed in claim 1, wherein said mixture of substances in the form of powder comprises a cross-linked amphiphilic polymer and a drug, obtained by high energy comilling or by loading by solvent.

7. Process as claimed in claim 1, wherein said mixture of substances further comprises a bioadhesive substance selected from the group consisting of alginates, scleroglucans, chitosans, xanthans and silicone gel.

8. Process as claimed in claim 1, wherein said mixture of substances further comprises a high density substance selected from the group consisting of aluminum oxide, titanium dioxide, iron oxide, calcium carbonate and barium sulfate.

9. Process as claimed in claim 1, wherein said liquid is selected from the group consisting of water, aqueous solutions, organic solvents and their mixtures, saturated and unsaturated natural oils, semisynthetic and synthetic mono-, di- and triglycerides, liquid waxes, silicone oils, polyethylene glycols, polyglycolic glycerides, and polyglycols.

10. Process as claimed in claim 1, wherein the amount of liquid with respect to the mixture of substances in powder form ranges from 1 to 80% by weight.

11. Pharmaceutical compositions in the form of microparticles obtained by the process as claimed in claim 1, wherein said microparticles have spherical or almost-spherical form with a diameter ranging from 100 $\mu$m to 3 mm.

12. Process as claimed in claim 1, further comprising the step of:

e) depositing a drug on the surface of the microparticles.

13. Process as claimed in claim 3, wherein said drug is selected from the group consisting of nifedipine and nicardipine.

14. Process as claimed in claim 4 wherein said drug and said cross-linked polymer are present in a ratio of from about 1:3 to about 1:5.

15. Process as claimed in claim 1 wherein said cross-linked amphiphilic polymers do not contain ionizable functional groups.

* * * * *